(12) United States Patent
Sarkar (10) Patent No.: US 10,937,162 B2
(45) Date of Patent: Mar. 2, 2021

(54) IMAGE ANALYSIS ALGORITHMS USING CONTROL SLIDES

(71) Applicant: Ventana Medical Systems, Inc., Tucson, AZ (US)

(72) Inventor: Anindya Sarkar, Milpitas, CA (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 138 days.

(21) Appl. No.: 16/119,520

(22) Filed: Aug. 31, 2018

(65) Prior Publication Data

US 2019/0026895 A1    Jan. 24, 2019

Related U.S. Application Data

(63) Continuation of application No. PCT/US2017/020245, filed on Mar. 1, 2017.

(60) Provisional application No. 62/464,972, filed on Feb. 28, 2017, provisional application No. 62/302,062, filed on Mar. 1, 2016.

(51) Int. Cl.
| | |
|---|---|
| *G06T 7/00* | (2017.01) |
| *G06K 9/62* | (2006.01) |
| *A61B 5/00* | (2006.01) |
| *G06T 7/73* | (2017.01) |
| *G06T 7/90* | (2017.01) |
| *G16H 30/40* | (2018.01) |

(52) U.S. Cl.
CPC ............ *G06T 7/0014* (2013.01); *A61B 5/00* (2013.01); *G06K 9/6206* (2013.01); *G06K 9/6211* (2013.01); *G06T 7/74* (2017.01); *G06T 7/90* (2017.01); *G06K 2209/05* (2013.01); *G06T 2207/10024* (2013.01); *G06T 2207/30004* (2013.01); *G06T 2207/30072* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 9,916,515 B2* | 3/2018 | Vink | G06T 7/0012 |
| 10,209,165 B2* | 2/2019 | Grunkin | G06K 9/0014 |
| 10,504,224 B1* | 12/2019 | Aeffner | G01N 33/574 |

(Continued)

FOREIGN PATENT DOCUMENTS

| | | | | |
|---|---|---|---|---|
| WO | 2009/072098 A1 | 6/2009 | | |
| WO | WO-2014140085 A1 * | 9/2014 | | G06T 7/11 |

(Continued)

*Primary Examiner* — Michelle M Entezari
(74) *Attorney, Agent, or Firm* — Kilpatrick Townsend and Stockton LLP (57) ABSTRACT

Systems and methods for automatically excluding artifacts from an analysis of a biological specimen image are disclosed. An exemplary method includes obtaining an immunohistochemistry (IHC) image and a control image, determining whether the control image includes one or more artifacts, upon a determination that the control image includes one or more artifacts, identifying one or more artifact regions within the IHC image by mapping the one or more artifacts from the control image to the IHC image, and performing image analysis of the IHC image where any identified artifact regions are excluded from the image analysis.

20 Claims, 8 Drawing Sheets

(56) References Cited

U.S. PATENT DOCUMENTS

| | | | |
|---|---|---|---|
| 2003/0118222 A1* | 6/2003 | Foran | G06K 9/00 |
| | | | 382/128 |
| 2005/0123181 A1 | 6/2005 | Freund et al. | |
| 2007/0237714 A1* | 10/2007 | Alvarez | A61K 31/00 |
| | | | 424/1.69 |
| 2008/0258907 A1* | 10/2008 | Kalpaxis | G08B 21/088 |
| | | | 340/539.1 |
| 2011/0235884 A1* | 9/2011 | Schreibmann | G06T 7/30 |
| | | | 382/131 |
| 2011/0320149 A1* | 12/2011 | Lee | H01L 22/12 |
| | | | 702/83 |
| 2012/0115752 A1* | 5/2012 | Zichi | C12N 15/1048 |
| | | | 506/9 |
| 2012/0257811 A1* | 10/2012 | Metzger | G06T 7/0012 |
| | | | 382/133 |
| 2012/0259574 A1* | 10/2012 | Hu | H01L 22/20 |
| | | | 702/117 |
| 2014/0233797 A1 | 8/2014 | Hodder et al. | |
| 2014/0270457 A1* | 9/2014 | Bhargava | G06T 7/0014 |
| | | | 382/133 |
| 2015/0004630 A1* | 1/2015 | Lange | G01N 33/5005 |
| | | | 435/7.21 |
| 2016/0042511 A1 | 2/2016 | Chukka et al. | |
| 2016/0166229 A1* | 6/2016 | Matthews | A61B 6/501 |
| | | | 600/431 |
| 2016/0283768 A1* | 9/2016 | Kounavis | G06K 9/00389 |

FOREIGN PATENT DOCUMENTS

| | | |
|---|---|---|
| WO | 2015052128 A1 | 4/2015 |
| WO | 2015/124777 A1 | 8/2015 |
| WO | 2017151799 A1 | 9/2017 |

\* cited by examiner

IMAGE ANALYSIS ALGORITHMS USING CONTROL SLIDES

CROSS-REFERENCE TO RELATED APPLICATIONS

This patent application is a continuation of International Patent Application No. PCT/US2017/020245 filed Mar. 1, 2017, which claims priority to and the benefit of U.S. Provisional Patent Application No. 62/302,062, filed Mar. 1, 2016 and U.S. Provisional Patent Application No. 62/464,972, filed Feb. 28, 2017. Each of the above patent applications is incorporated herein by reference as if set forth in its entirety.

FIELD OF THE INVENTION

The present disclosure generally relates to the field of medical imaging. Some examples discussed in the present disclosure relate to methods of automatically detecting and excluding artifacts from image analysis of images of biological specimens.

BACKGROUND AND RELATED ART

In the analysis of biological specimens such as tissue sections, cytology images, tissue microarray (TMA) images, cell lines, blood smears, and the like, the biological specimens are sometimes stained with one or more different stains or dyes in order to highlight various types of structures within the specimen, such as specific types of tissue, cells, cell organelles, and so forth. This can enable pathologists and other health care professionals to better assess the specimen's morphology and deliver a more accurate diagnosis, prognosis, and treatment plan for the patient.

One method of staining the specimen is hematoxylin and eosin (H&E) staining, in which a dark blue or violet hematoxylin binds to basophilic substances such as DNA and RNA, and a red or pink eosin binds to acidophilic substances such as positively charged amino acid side chains. Thus, cell nuclei on specimen slides stained with H&E are likely to appear in blue or purple, while structures like the cytoplasm, basophils, muscles, erythrocytes, collagen, and mitochondria are likely to appear in different shades of pink or red.

In situ hybridization (ISH) staining is a technique that uses a labeled complementary DNA, RNA or modified nucleic acids strand (i.e., probe) to localize a specific DNA or RNA sequence in a portion or section of tissue. In situ hybridization can be a powerful technique for identifying specific mRNA species within individual cells in tissue sections, providing insights into physiological processes and disease pathogenesis.

Immunohistochemistry (IHC) staining is another staining technique that has become popular due to its significant efficiencies and the rich diagnostic information that it generates. IHC slide staining can be utilized to identify proteins in cells of a tissue section and hence is widely used in the study of different types of cells, such as cancerous cells and immune cells in biological tissue. For example, IHC staining may be used in research and clinical settings to understand the distribution and localization of the differentially expressed biomarkers of immune cells in a cancerous tissue for an immune response study. For example, tumors often contain infiltrates of immune cells, which may prevent the development of tumors or favor the outgrowth of tumors. In this scenario, multiple stains may be used to target different types of immune cells, and the population distribution of each type of immune cell is used in studying the clinical outcome of the patients.

Researchers and clinicians have traditionally examined tissue slides stained with H&E, IHC, ISH, fluorescent ISH (FISH), or other methods under a bright-field or a fluorescence microscope. However, as the assays are becoming more complicated and often require locating and counting of hundreds or thousands of cells of specific types in specific types of regions, performing these tasks manually (and accurately) becomes an increasingly difficult task. Accordingly, more and more researchers and clinicians are beginning to employ "digital pathology" solutions that can help them get faster, more accurate, and more reproducible results. Digital pathology systems include slide scanners that can scan tissue slides to produce very high resolution (e.g., 0.5 or 0.275 microns per pixel) digital images of the tissue. Digital pathology systems also include hardware and/or software solutions for automatically processing, viewing, segmenting, analyzing (e.g., scoring) and otherwise managing tissue images or other types of biological specimen images.

As part of immunohistochemistry (IHC) staining protocol, one or more negative and/or positive control slides are often prepared, stained, and scanned for the purpose of validating the quality of the staining process. For example, a negative control slide can include an adjacent tissue section prepared in the same way as the tissue on the main IHC slide, with the exception that the primary antibody is either omitted or replaced with some other solution such as isotype, tissue culture media, buffer, or dilute non-immune serum of the same species as the primary antibody. Such slides can be used, for example, to determine the level of background stain and make sure that it does not exceed acceptable limits.

SUMMARY

Disclosed herein are systems and methods for automatically excluding artifacts from an analysis of a biological specimen image.

In some embodiments, an image analysis system for analyzing biological specimen images is disclosed. The system may include an image registration engine that can be configured to obtain an immunohistochemistry (IHC) image and a control image, and to determine whether the IHC image and the control image are structurally similar. The system may also include an artifact detection engine configured to determine whether the control image includes one or more artifacts, and upon a determination that the control image includes one or more artifacts, to identify one or more artifact regions within the IHC image by mapping the one or more artifacts from the control image to the IHC image. The system may further include, among other things, an image analysis engine configured to perform an image analysis of the IHC image, where the one or more artifact regions are excluded from the image analysis based on a determination that the IHC image and the control image are structurally similar.

In other embodiments, a method of detecting and excluding artifact regions from image analysis is disclosed. The method may include, among other things, obtaining an immunohistochemistry (IHC) image and a control image; determining whether the control image includes one or more artifacts; upon a determination that the control image includes one or more artifacts, identifying one or more artifact regions within the IHC image by mapping the one or more artifacts from the control image to the IHC image; and performing an image analysis of the IHC image, wherein the one or more artifact regions are excluded from the image analysis.

In yet other embodiments, a non-transitory computer-readable medium storing instructions is disclosed. The instructions, when executed by a processor of an image analysis system, may cause the image analysis system, for example, to obtain a field of view (FOV) of an immunohistochemistry (IHC) image of an IHC slide; obtain a control image of a control slide associated with the IHC slide; map the FOV from the IHC image to the control image to obtain a control FOV; detect artifacts within the control FOV; and notify a user if any artifacts have been detected in the control FOV.

These and other embodiments are discussed in more detail below.

BRIEF DESCRIPTION OF THE DRAWINGS

In the following embodiments of the invention are explained in greater detail, by way of example only, making reference to the drawings in which.

DETAILED DESCRIPTION

As mentioned above, digital pathology solutions may enable the automatic processing and analysis of an IHC image. Unfortunately, various tissue artifacts may appear on the IHC image similar in color, shape, and intensity, to a positive stain such as DAB. Such artifacts can be falsely identified by the image analysis algorithm as stained cells, which can cause the algorithm to produce incorrect results such as inaccurate counts of various types of cells.

Methods and systems described herein are directed to using previously unutilized control slides to identify regions in the IHC image that contain artifacts and excluding those areas from the analysis, thereby improving the algorithm's overall accuracy. Such methods and systems can be especially beneficial when applied to whole-slide-analysis workflows, where the pathologist cannot avoid the artifact problem by finding a field of view (FOV) free of artifacts. However, the techniques discussed herein can also improve an FOV-based workflow, because some artifacts can appear so substantially similar to a positive IHC stain, that distinguishing them from the positive stain based on an IHC image alone can be a very time consuming and difficult (if not impossible) task even for trained pathologists.

More specifically, the methods and systems disclosed herein can be used to detect and exclude artifacts that appear on both the IHC slide and the adjacent control slides. Such artifacts may include, for example, tissue pigments (e.g., melanin, hemosiderin, etc.) or other artifacts associated with the tissue itself.

The methods and systems discussed herein can be applied to positive control slides as well as negative control slides, both types being collectively referred to herein as "control slides." Because a control slide is typically stained with a single stain (e.g., blue hematoxylin for negative control, and brown DAB for positive control), any pixel or region in the control slide image whose color falls outside of the expected color range associated with that stain is likely to be an artifact.

Figure 1:
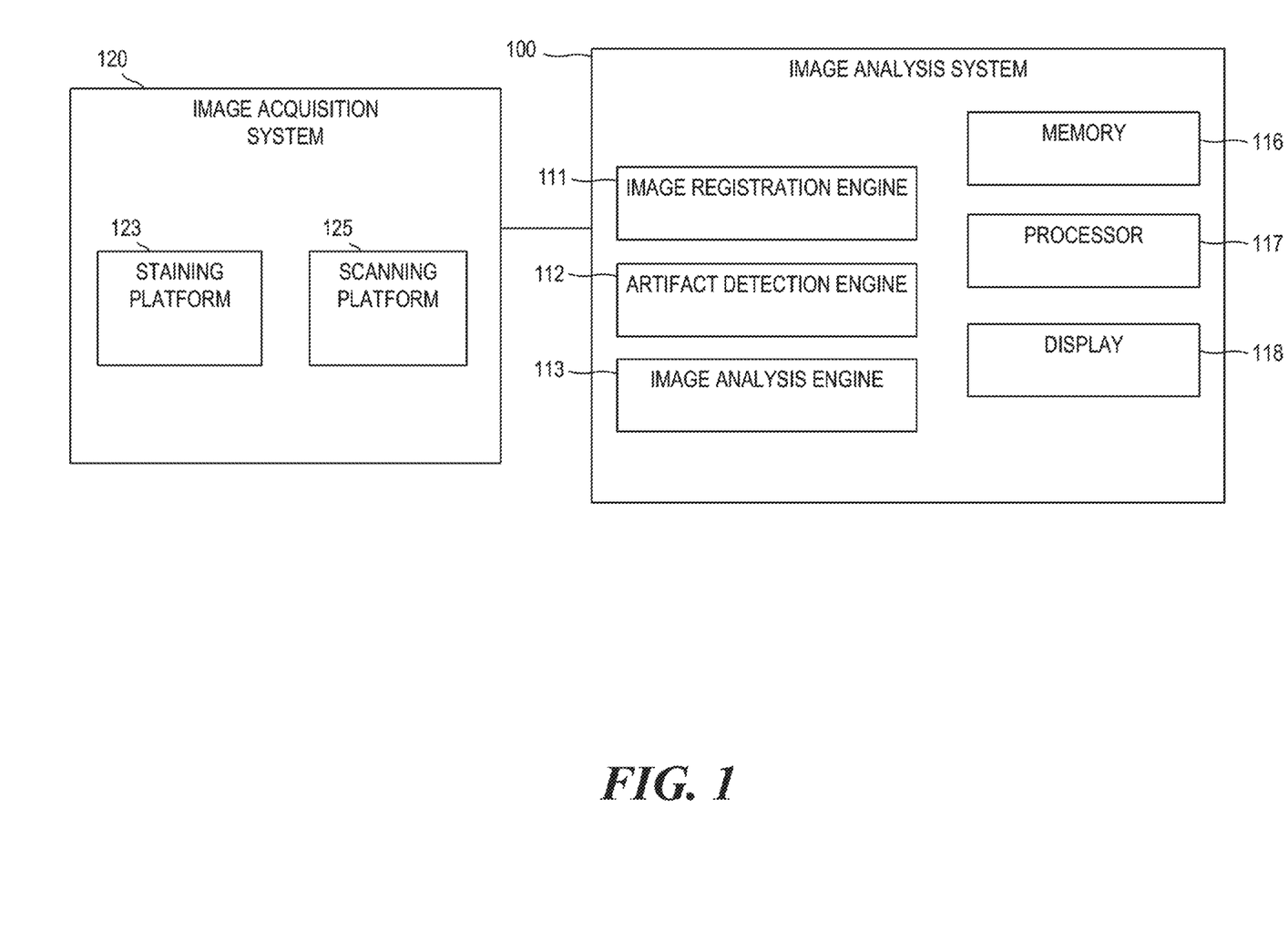
FIG. 1 shows an exemplary image acquisition system and an exemplary image analysis system, in accordance with some embodiments.

FIG. 1 is a block diagram of an image analysis system 100, according to an exemplary embodiment of the subject disclosure. Image analysis system 100 may include one or more computing devices such as desktop computers, laptop computers, tablets, smartphones, servers, application-specific computing devices, or any other type(s) of electronic device(s) capable of performing the techniques and operations described herein. In some embodiments, image analysis system 100 may be implemented as a single device. In other embodiments, image analysis system 100 may be implemented as a combination of two or more devices together achieving the various functionalities discussed herein. For example, image analysis system 100 may include one or more server computers and a one or more client computers communicatively coupled to each other via one or more local-area networks and/or wide-area networks such as the Internet.

As illustrated in FIG. 1, image analysis system 100 may include a memory 116, a processor 117, and a display 118. Memory 116 may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. For brevity purposes memory 116 is depicted in FIG. 1 as a single device, but it is appreciated that memory 116 can also be distributed across two or more devices.

Processor 117 may include one or more processors of any type, such as central processing units (CPUs), graphics processing units (GPUs), special-purpose signal or image processors, field-programmable gate arrays (FPGAs), tensor processing units (TPUs), and so forth. For brevity purposes processor 117 is depicted in FIG. 1 as a single device, but it is appreciated that processor 117 can also be distributed across any number of devices.

Display 118 may be implemented using any suitable technology, such as LCD, LED, OLED, TFT, Plasma, etc. In some implementations, display 118 may be a touch-sensitive display (a touchscreen).

As illustrated in FIG. 1, image analysis system 100 may also include an image registration engine 111, an artifact detection engine 112, and an image analysis engine 113. While these modules are depicted in FIG. 1 as standalone modules, it will be evident to persons having ordinary skill in the art that each module may instead be implemented as a number of sub-modules, and that in some embodiments any two or more modules can be combined into a single module. Furthermore, in some embodiments, system 100 may include additional engines and modules (e.g., input devices, networking and communication modules, etc.) not depicted in FIG. 1 for brevity. Furthermore, in some embodiments, some of the blocks depicted in FIG. 1 may be disabled or omitted. As will be discussed in more detail below, the functionality of any module of system 100 can be implemented in hardware, software, firmware, or as any combination thereof.

As depicted in FIG. 1, in some embodiments image analysis system 100 may be communicatively coupled to an image acquisition system 120. Image acquisition system 120 may obtain images of biological specimens and provide those images to image analysis system 100 for analysis and presentation to the user.

Image acquisition system 120 may include an automated staining platform 123 for staining biological specimen slides using H&E, IHC, ISH, FISH, or any other staining process. Commercially available staining platforms include, for example, HE 600, BENCHMARK XT, and BENCHMARK ULTRA products by Ventana Medical Systems, Inc. Image acquisition system 120 may also include a scanning platform 125 such as a slide scanner that can scan the stained slides at 20×, 40×, or other magnifications to produce high resolution whole-slide digital images. Commercially available slide scanners include, for example, VENTANA iScan HT and iScan Coreo products by Ventana Medical Systems, Inc.

Images generated by scanning platform 125 may be transferred to image analysis system 100 or to a server or database accessible by image analysis 100. In some embodiments, the images may be transferred automatically via one or more local-area networks and/or wide-area networks. In some embodiments, image analysis system 100 may be integrated with or included in scanning platform 125 and/or other modules of image acquisition system 120, in which case the image may be transferred to image analysis system, e.g., through a memory accessible by both platform 125 an system 120. In some embodiments, image acquisition system 120 may not be communicatively coupled to image analysis system 100, in which case the images may be stored on a non-volatile storage medium of any type (e.g., a flash drive) and downloaded from the medium to image analysis system 100 or to a server or database communicatively coupled thereto. In any of the above examples, image analysis system 100 may obtain an image of a biological sample, where the sample may have been affixed to a slide and stained by staining platform 123, and where the slide may have been scanned by a slide scanner or another type of scanning platform 125. It is appreciated, however, that in other embodiments, below-described techniques may also be applied to images of biological samples acquired through other means.

In some embodiments, image analysis system 100 may obtain and pass to image registration engine 111 a control image (an image of a negative control slide or a positive control slide) and an IHC image (an image of an IHC slide adjacent to the control slide). As used herein, "adjacent slides" refer to slides containing tissue sections that were cut from the same tissue block. In some embodiments, the two tissue sections can be the closest two sections that were cut from that block. In other embodiments, the two sections may not necessarily be the closest ones from that block, but may still be within sufficiently close proximity (e.g., within 10 μm or 20 μm) of each other.

After obtaining the control image and the IHC image, image registration engine 111 may align the two images in a process referred to as "registration." In some embodiments, engine 111 may use the following registration method to align the images. Suppose I1 represents the IHC image and I2 represents the control image. Let $\{x1,i, y1,i\}$ represent the i-th cell center for image I1. Similarly, let $\{x2,i, y2,i\}$ represent the i-th cell center for image I2. Suppose there have been N1 cells detected in image I1 and N2 cells detected in image I2. Let D(P1, P2) be the distance to be computed between two point sets P1 and P2, where P1=$\{x1,i,y1,i\}$ i=1, ..., i=N1 and P2=$\{x2,i,y2,i\}$i=1, ..., i=N2, corresponding to I1 and I2, respectively.

In some embodiments, to compensate for a potential rotation, shift, and other type of special transformation (e.g., shear or reflection) between I1 and I2, engine 111 may calculate the affine transformation between the two images using Procrustes method or any other suitable method. After computing the transformation function, engine 111 may use it to transform point set P1 into a transformed point set P1'. D(P1, P2) can then be computed as the mean distance between every point in P2 and the nearest point in P1'. In other embodiments, engine 111 may instead transform point set P2 into a transformed point set P2' and compute D(P1, P2) as the mean distance between every point in P1 and the nearest point in P2'.

After computing the mean distance D(P1, P2), engine 111 may determine, based on the mean distance, whether images I1 and I2 are structurally similar. In some embodiments, "structurally similar" can mean that the location of most or all of the cell nuclei, TMA cores, needle biopsies, and/or any other types of objects of interest will be substantially similar in both images. In some embodiments, engine 111 may compare the mean distance D(P1, P2) to a predefined threshold and determine that the images are structurally similar if and only if the mean distance is below that predefined threshold.

Figure 2:
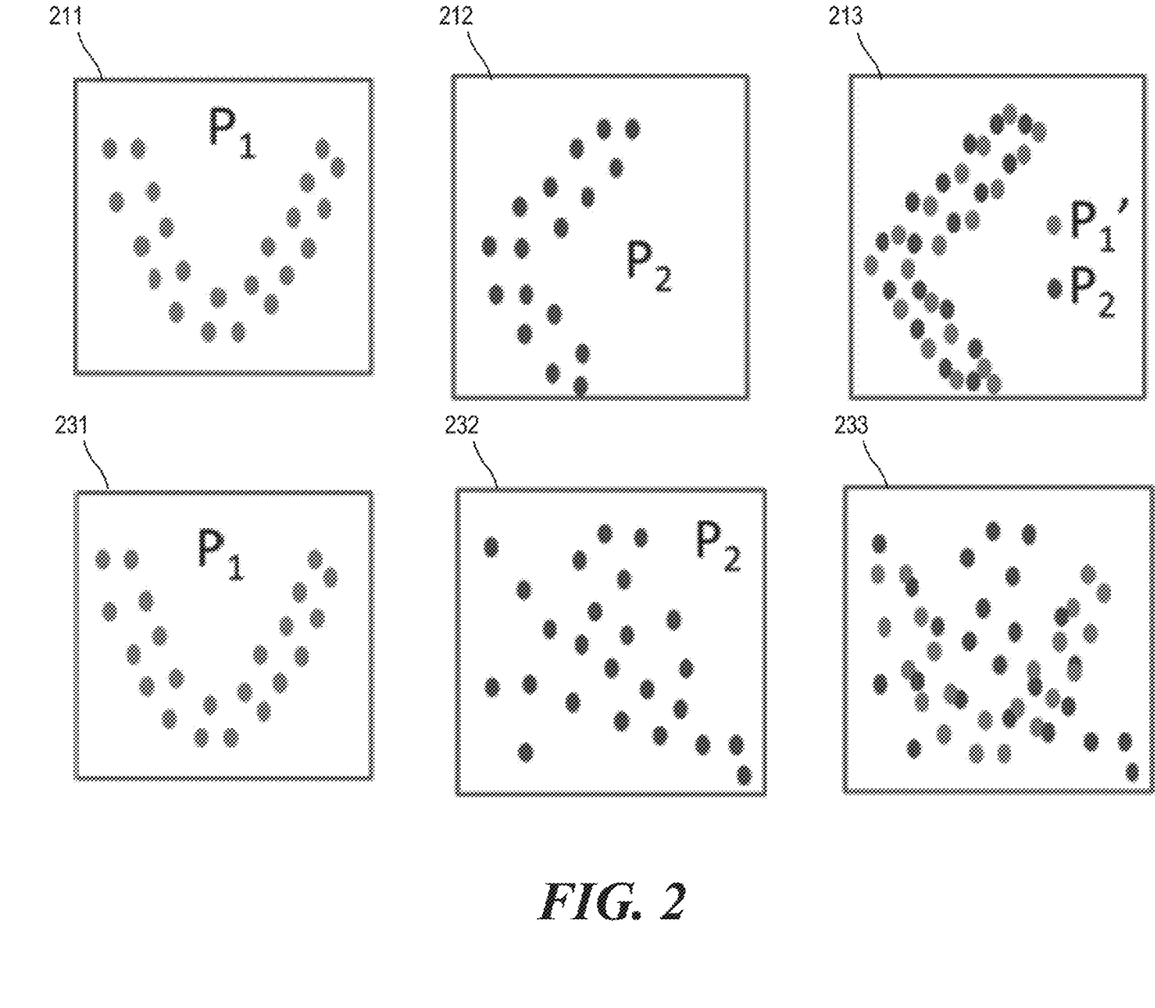
FIG. 2 shows various examples of image registration, in accordance with some embodiments.

To illustrate, FIG. 2 shows at the top row image 211 containing point set P1, adjacent image 212 containing point set P2, and image 213 that shows transformed (90-degree rotated) point set P1' overlaid upon point set P2. In this example, point sets P1' and P2 are well matched, indicating structural similarity between adjacent images 211 and 212. In contrast, at the bottom row FIG. 2 shows image 231 containing point set P1, adjacent image 232 containing point set P2, and image 233 that shows the two point sets overlaid on each other. It is apparent from this example that even the most optimal transformation function could not transform P1 such that it would match P2, i.e., such that D(P1, P2) would be relatively low. Accordingly, in this example there is probably no structural similarity between adjacent images 231 and 232.

In some embodiments, upon a determination by image registration engine 111 that the two images are structurally similar, artifact detection engine 112 may obtain the control image and process it to detect artifacts. In other embodiments, engine 112 may run the artifact detection process or portions thereof in parallel with the image registration process performed by image registration engine 111.

Artifact detection engine 112 can use any suitable algorithm to detect artifacts in the control image. In one embodiment, the artifacts can be detected using an intensity-based thresholding method. For example, engine 112 may obtain a grayscale version of a negative control image and determine that higher intensity pixels (e.g., pixels whose intensity is higher than a predefined threshold) correspond to counterstain regions, while the rest of the pixels (e.g., pixels whose intensity is lower or equal to the predefined threshold) correspond to artifacts. In another example, engine 112 may obtain a grayscale version of a positive control image and determine that lower intensity pixels (e.g., pixels whose intensity is lower than a first threshold) correspond to positively stained regions; higher intensity pixels (e.g., pixels whose intensity is higher than a second threshold) correspond to the image background, and that the rest of the pixels (e.g., pixels whose intensity is between the first and the second thresholds) correspond to artifacts.

In another embodiment, artifact detection engine 112 may obtain (e.g., from memory 116 or via input from the user) a predefined color range corresponding to all possible non-artifact colors (e.g., counter-stain colors in negative control slides or stain colors in positive control slides). The predefined color range may be defined, for example, in a one-dimensional, two-dimensional, or three-dimensional space (e.g., the LAB color space), where a one-dimensional color range can also be referred to as an intensity range. After obtaining the predefined color/intensity range, engine 112 may determine that any pixels whose color/intensity falls outside of the predefined color/intensity range are artifacts. In other embodiments, engine 112 may also obtain a color/intensity range representing the background, and determine that any pixels whose color/intensity range falls outside both the predefined color/intensity range and the background color/intensity range are artifacts. In some embodiments, instead of obtaining predefined color/intensity ranges corresponding to the stain, the counter-stains, and/or the background, engine 112 may analyze the control image and automatically determine these ranges, for example, by finding one or two highest peaks on the color/intensity histogram, and establishing that the peaks correspond to the background and either the stain or the counter-stain.

After determining the locations of the artifacts (e.g., locations of regions containing only or mostly artifact pixels), artifact detection engine 112 can map all artifact candidates from the control image onto the IHC image using, for example, the transformation function computed by image registration engine 111 (discussed above). After the artifacts are mapped onto the IHC image, artifact mapping engine 112 may pass the locations of the artifacts on the IHC image to image analysis engine 113.

After image analysis engine 113 obtains the locations of the artifacts on the IHC image, it may exclude such artifacts from its analysis. In other words, when image analysis engine 113 subsequently runs an image analysis algorithm on the IHC image, it may disregard any artifact, or any region containing an artifact or at least a predefined percentage of artifacts. The term "region" as used herein can correspond, for example, to an area of a predefined size, such as a circle of a predefined radius, a rectangle of a predefined size (e.g., a slide tile or an FOV), and so forth.

In some embodiments, after the artifact regions on the IHC image are identified, analysis engine 113 may highlight or outline those regions on display 118, thereby allowing the user to modify the regions, e.g., by making them larger or smaller, by manually drawing additional regions, by cancelling some of the identified regions (i.e., marking them as non-artifact regions), and so on.

After the artifact regions are identified and optionally modified by the user, image analysis engine 113 can perform the image analysis on the IHC image while excluding those regions from the analysis. For example, the image analysis may be a whole-slide scoring algorithm that counts various types of cells (e.g., all or a certain type of stained and/or unstained cells), their intensities, ratios, etc., throughout the entire slide or at least a large portion (e.g., >50%) of the area covered by tissue. Excluding (i.e., disregarding) the artifact regions from the algorithm's calculations can improve the algorithm's accuracy, because the algorithm could have falsely identified some artifacts as stained cells or other types of significant objects.

Figure 3:
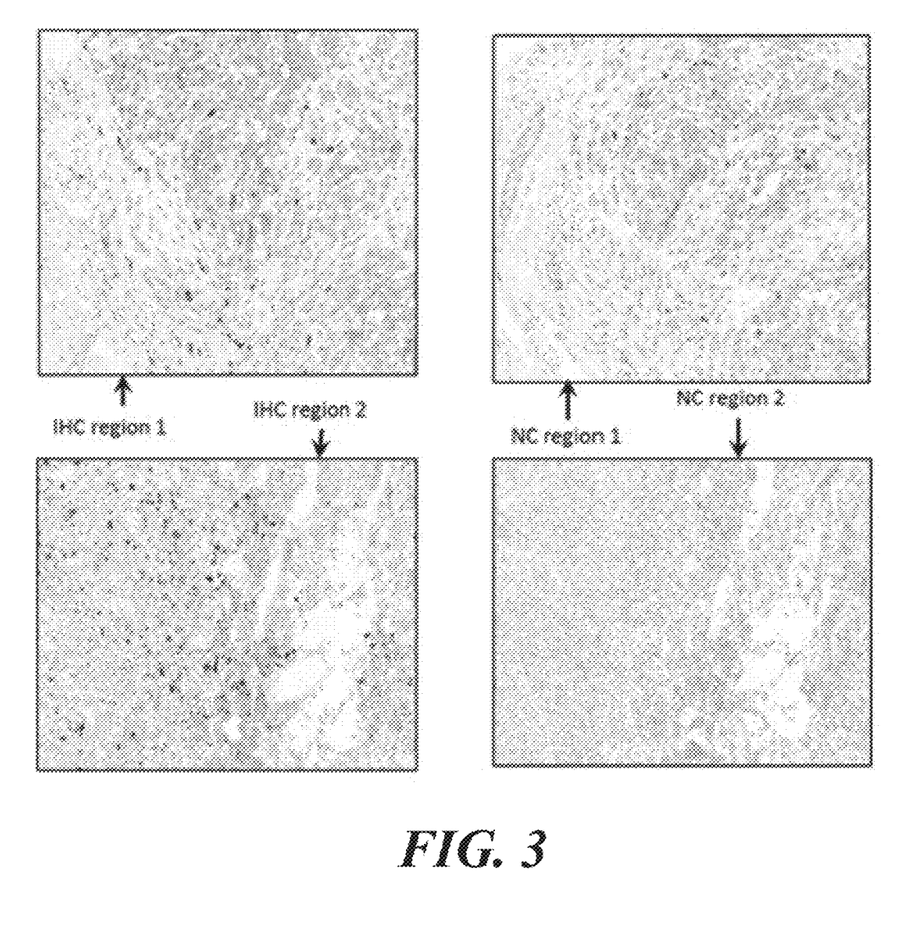
FIG. 3 shows examples of regions of IHC and negative control (NC) images.
Figure 4:
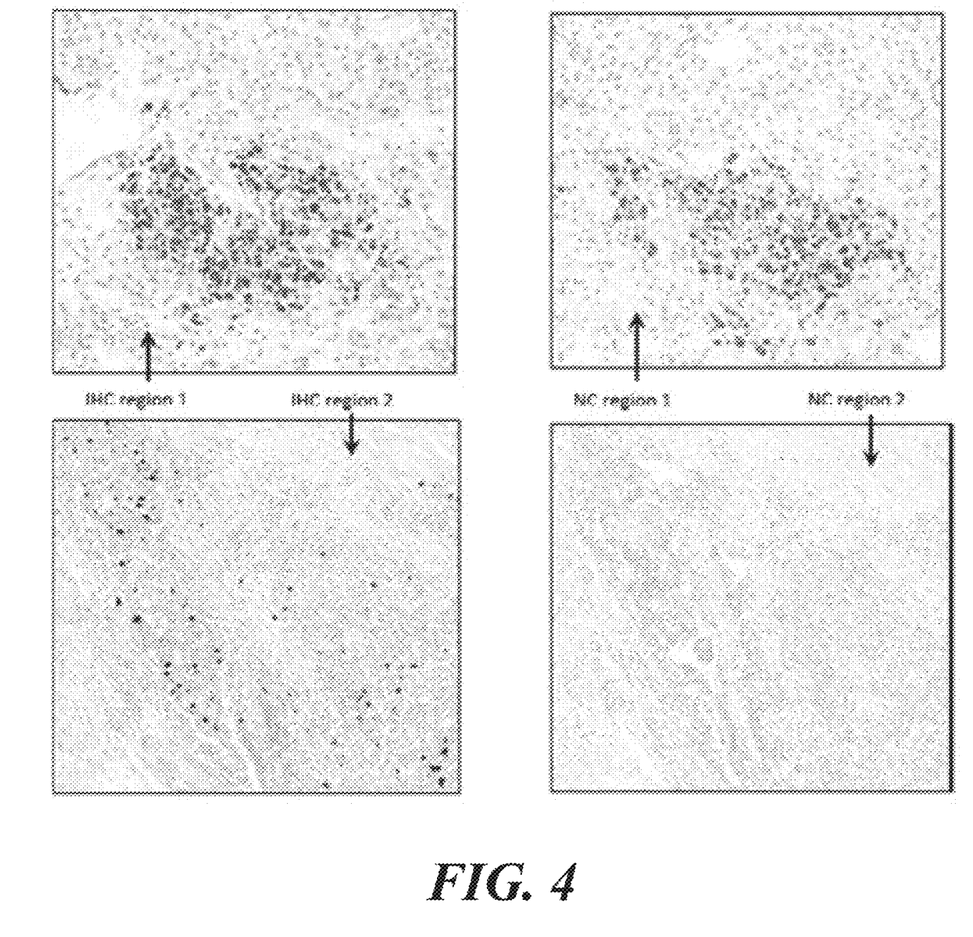
FIG. 4 shows other examples of regions of IHC and NC images.
Figure 5:
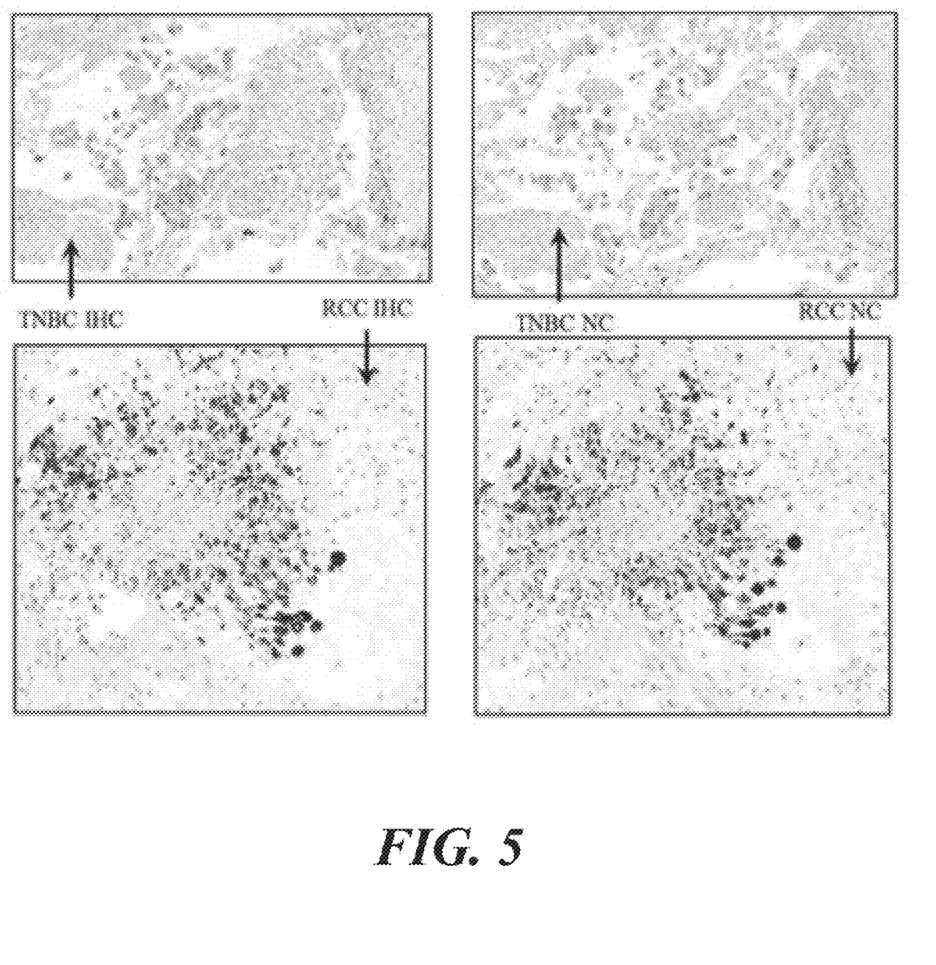
FIG. 5 shows yet other examples of regions of IHC and NC images.

FIGS. 3-5 illustrate some of the methods described above using by showing various samples with different types of artifacts. FIG. 3 shows two regions of a melanoma specimen, where region 1 of the negative control (NC) image has dark spots attributable to melanin, while region 2 of the NC image has no such spots. Accordingly, in this example, if the IHC image is determined by image registration engine 111 to be structurally similar to the adjacent NC image, melanin pigments detected in region 1 of the NC image by artifact detection engine 112 will be mapped by that engine into a corresponding region 1 of the IHC image (top left) and the entire region can be excluded by image analysis engine 113 when it runs a whole-slide image analysis algorithm on the IHC image. This is advantageous, because many of the dark spots in region 1 of the IHC image are likely also attributable to melanin and not a positive DAB stain. In contrast, artifact detection engine 112 in this example will not detect any dark spots in region 2 of the NC image. Therefore, the dark spots on mapped region 2 on the IHC image (bottom left) are all likely attributable to DAB stain, and the region will not be excluded and will be analyzed by the image processing algorithm.

Similarly, FIG. 4 shows an example of pigment detection in renal cell carcinoma (RCC) where region 1 contains hemosiderin pigment and region 2 does not. To further illustrate the wide range of artifacts that can be detected and excluded from analyses using the methods and systems described herein, FIG. 5 shows two additional NC regions, one of a triple negative breast cancer (TNBC) sample and one from a renal cell carcinoma (RCC) sample. In this example, both NC regions contain pigment, meaning that both regions would be mapped onto the IHC image and thereafter excluded from the whole-slide analyses of their respective IHC images.

Figure 6:
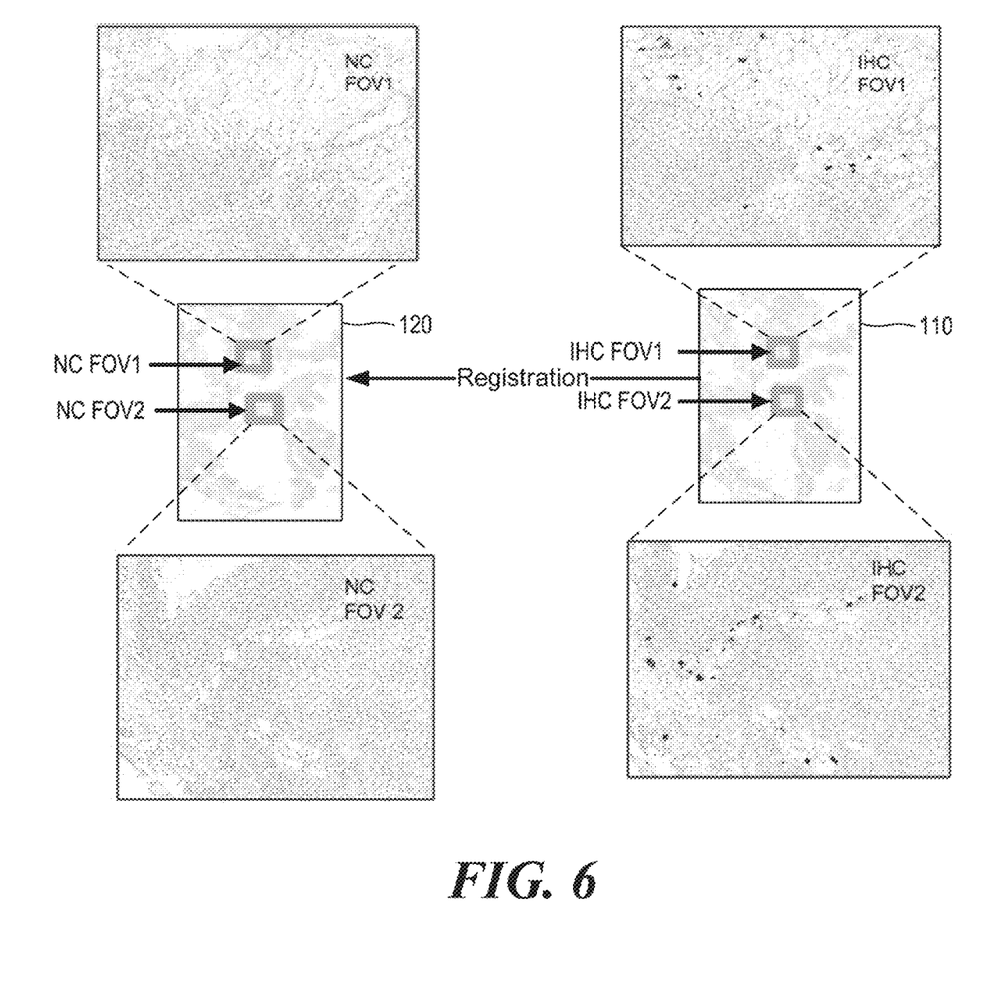
FIG. 6 illustrates an FOV-based workflow, in accordance with some embodiments.

In some embodiments, the techniques discussed above can also be applied to FOV-based algorithms, where the user selects (e.g., on an IHC image) one or more FOVs where the user wishes to run the image analysis algorithm. For example, image registration engine 111 can use the above-discussed techniques to determine whether the IHC image and the adjacent control slide are structurally similar. If so, artifact engine 112 can use the above-discussed techniques to map the selected FOVs from the IHC image onto the adjacent control slide, and to determine whether the mapped FOVs of the control slide include any artifacts (or an amount/percentage of artifacts that exceeds a predefined threshold). Image analysis engine 113 can then notify the user about every FOV that includes artifacts, and allow the user to select another FOV instead. FIG. 6 illustrates an example IHC image 610, an adjacent NC image 620, and two FOVs (FOV1 and FOV2) mapped from IHC image to adjacent NC image 620. In this example, neither of the NC FOVs appear to have any dark stain, meaning that all the stain in the corresponding IHC FOVs is likely attributable to DAB stain and not to artifacts such as pigment.

Figure 7:
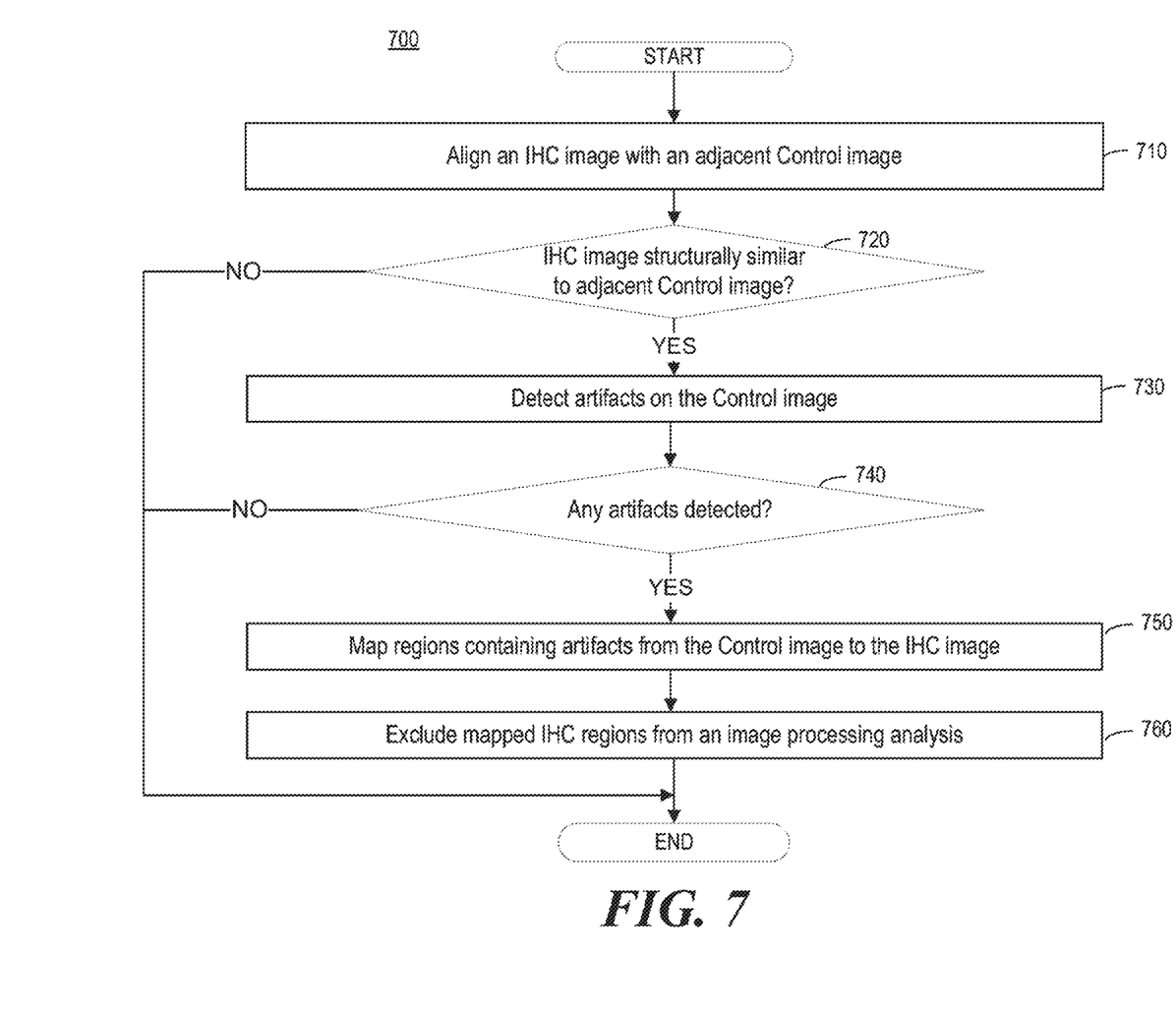
FIG. 7 shows an exemplary method of automatically detecting and excluding artifact regions from image analysis, such as a whole-slide image analysis, in accordance with some embodiments.

FIG. 7 illustrates a flowchart of an exemplary method 700 for automatically (without any input from the user) detecting and excluding artifact regions from an image analysis (e.g., a whole-slide image analysis). Method 700 may be executed, for example, by various modules of image analysis system 100 discussed above. Method 700 may be implemented, for example, in the form of executable instructions stored on at least one non-transitory machine-readable storage medium (e.g., memory 116) and executed by at least one processor or processor core (e.g., processor 117). Method 700 may also be implemented in the form of electronic circuitry (e.g., hardware), or in the form of some combination of electronic circuitry and instructions executable by a processor. It will be appreciated by persons skilled in the art based on the following description of method 700 that some blocks of method 700 may be executed substantially concurrently or in a different order than shown in FIG. 7 (e.g., steps 710 and 720 may sometimes be performed concurrently or after steps 730 and 740); that method 700 may include more or less blocks than are shown in FIG. 7; and that some blocks of method 700 may, at certain times, be ongoing and/or may repeat.

Method 700 may begin at block 710 where an IHC image can be aligned with an adjacent control image, as discussed above. At block 720, it may be determined whether or not the IHC image is structurally similar to the adjacent control image. If so, at block 730 artifacts may be detected on the control image. At block 740, it may be determined whether any artifacts have been detected. If so, at block 750, regions containing artifacts can be mapped from the control image to the IHC image, and at block 760 the mapped IHC regions can be excluded from the whole-slide image analysis.

Figure 8:
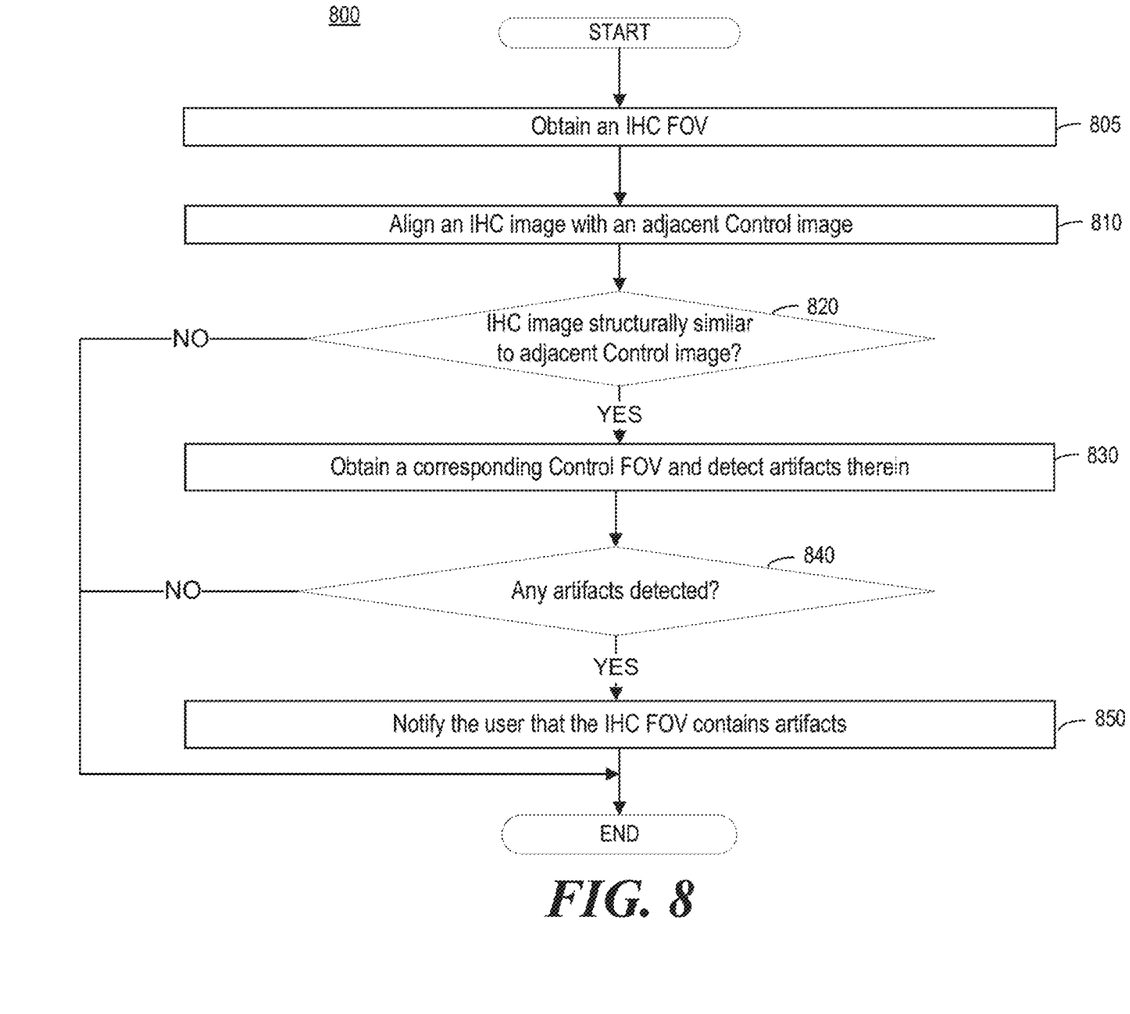
FIG. 8 shows an exemplary method of automatically detecting artifacts in an FOV, in accordance with some embodiments.

As mentioned above, the order of the steps of method 700 is not limiting, and in various embodiments, some steps of the method can be performed in a different order and/or in parallel. For example, in some embodiments, the artifact detection can firm be performed on the control image, and only if some artifact regions are detected, the IHC image and the control image can be registered. After the images are registered, each artifact region can be mapped from the control image to the IHC image, and a structural similarity between the images can be determined. In this embodiment, FIG. 8 illustrates a flowchart of an exemplary method 800 for automatically (without any input from the user) detecting artifacts in an FOV. Method 800 may be executed, for example, by various modules of image analysis system 100 discussed above. Method 800 may be implemented, for example, in the form of executable instructions stored on at least one non-transitory machine-readable storage medium (e.g., memory 116) and executed by at least one processor or processor core (e.g., processor 117). Method 800 may also be implemented in the form of electronic circuitry (e.g., hardware), or in the form of some combination of electronic circuitry and instructions executable by a processor. It will be appreciated by persons skilled in the art based on the following description of method 800 that some blocks of method 800 may be executed substantially concurrently or in a different order than shown in FIG. 8; that method 800 may include more or less blocks than are shown in FIG. 8; and that some blocks of method 800 may, at certain times, be ongoing and/or may repeat.

Method 800 may begin at block 805 where an FOV may be obtained (e.g., selected by the user) on an IHC image. At block 810, the IHC image may be aligned with an adjacent control image using a whole-slide registration method. At block 820, it may be determined whether or not the IHC image is structurally similar to the control image. If so, at block 830, the IHC FOV can be mapped onto the control image to determine a control FOV, which can then be analyzed for artifacts. At block 840, it may be determined whether or not any artifacts were detected in the control FOV. If so, at block 850, the user can be notified that the IHC FOV contains some artifacts, i.e., some stain attributable to artifacts and not to a biomarker.

In the foregoing discussion, various devices, engines, units, or blocks (e.g., engines 111, 112, and 113) were described as being implementable using hardware, software, firmware, or any combination thereof. It must be appreciated by a person skilled in the art in view of the foregoing discussion that the hardware may include any type of analog and/or digital circuitry, such as integrated circuits (IC) (e.g., application-specific integrated circuits (ASICs) or field-programmable gate arrays (FPGAs)), or any other type of special- or general-purpose electronic circuitry. It must be further appreciated by a person skilled in the art that the software or firmware may include any type of processor executable instructions that can be stored on any type of tangible non-transitory computer-readable medium, where the instructions can be executed by a processing resource, causing the processing resource to implement the functionality of the respective component.

The executable instructions can be stored in memory 116, or in any other non-transitory computer-readable storage medium, which can be implemented as any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. The non-transitory computer-readable medium can be integrated in the same device as the processor resource or it may be separate but accessible to that device and the processor resource. In one example, the program instructions can be part of an installation package that when installed can be executed by the processor resource to implement the corresponding component. In this case, the computer-readable medium may be a portable medium such as a CD, DVD, or flash drive or a memory maintained by a server from which the installation package can be downloaded and installed. In another example, the program instructions may be part of an application or applications already installed, and the computer-readable medium may include integrated memory such as a hard drive, solid state drive, random access memory (RAM), read-only memory (ROM), and the like.

The processing resource for executing the instructions can be, for example, processor 117, or it can be any other processing resource, such as a CPU, a GPU, an FPGA, a TPU, another type of processor configured to retrieve and execute instructions, or a combination thereof. The processing resource can be integrated in a single device or distributed across devices, which may be integrated with image analysis system 100 or communicatively coupled to image analysis system 100.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. An image analysis system for analyzing biological specimen images, the image analysis system comprising:
   an image registration engine configured to:
   obtain an immunohistochemistry (IHC) image and a control image;
   perform a registration operation to align the IHC image and the control image to a single coordinate system;
   as a result of the IHC image and the control image being aligned to the single coordinate system based on the registration operation, identify a distance metric between an image object of the IHC image to a corresponding image object of the control image, wherein the image object of the IHC image and the corresponding image object of the control image correspond to a same tissue type;
   determine that the identified distance metric is below a predefined threshold; and
   in response to determining that the identified distance metric is below the predefined threshold, determine that the IHC image and the control image are structurally similar;
   an artifact detection engine configured to:
   receive, from the image registration engine, an indication that the IHC image and the control image are structurally similar;
   determine that the control image includes one or more artifacts that are falsely identifiable as stained cells during an image analysis of a plurality of regions of the IHC image; and
   in response to the indication received from the image registration engine and the determination that the control image includes the one or more artifacts, identify one or more artifact regions within the IHC image by mapping a region of the control image that includes the one or more artifacts to a corresponding region of the IHC image; and
   an image analysis engine configured to perform the image analysis of the plurality of regions of the IHC image except for the one or more artifact regions within the IHC image.

2. The image analysis system of claim 1, wherein the IHC image and the control image include tissue sections of a same biological specimen block.

3. The image analysis system of claim 1, wherein the image analysis comprises a whole-slide scoring algorithm.

4. The image analysis system of claim 1, wherein the IHC image corresponds to a tissue slide stained with a stain of a first color, wherein the one or more artifacts of the control image have a second color, and wherein the first color is substantially similar to the second color.

5. The image analysis system of claim 1, wherein the control image corresponds to one of a negative control slide or a positive control slide, and wherein the one or more artifacts of the control image comprise pigments.

6. The image analysis system of claim 1, wherein the registration operation comprises transforming the IHC image or the control image using an affine transformation.

7. The image analysis system of claim 1, wherein the control image is an image of a negative control slide stained with a counter-stain, and wherein the determining that the control image includes the one or more artifacts comprises determining pixels in the control image fall outside of a color range associated with the counter-stain.

8. The image analysis system of claim 7, wherein the color range is either predefined or dynamically computed based on the control image.

9. The image analysis system of claim 1, wherein the image analysis engine is further configured to highlight the one or more artifact regions on a display.

10. The image analysis system of claim 9, wherein the image analysis engine is further configured to modify the one or more artifact regions based on a user input.

11. A method of detecting and excluding artifact regions from image analysis, the method comprising:
    obtaining an immunohistochemistry (IHC) image and a control image;
    performing a registration operation to align the IHC image and the control image to a single coordinate system;
    as a result of the IHC image and the control image being aligned to the single coordinate system based on the registration operation, identifying a distance metric between an image object of the IHC image to a corresponding image object of the control image, wherein the image object of the IHC image and the corresponding image object of the control image correspond to a same tissue type;
    determining that the distance metric is below a predefined threshold;
    in response to determining that the identified distance metric is below the predefined threshold, determining that the IHC image and the control image are structurally similar;
    determining that the control image includes one or more artifacts that are falsely identifiable as stained cells during an image analysis of a plurality of regions of the IHC image;
    in response to determining that the identified distance metric is below the predefined threshold and that the control image includes the one or more artifacts, identifying one or more artifact regions within the IHC image by mapping a region of the control image that includes the one or more artifacts to a corresponding region of the IHC image; and
    performing the image analysis of the plurality of regions of the IHC image except for the one or more artifact regions.

12. The method of claim 11, wherein performing the registration operation comprises transforming the IHC image or the control image using an affine transformation.

13. The method of claim 11, wherein the image analysis includes performing a whole-slide scoring algorithm.

14. The method of claim 11, wherein the control image is an image of a negative control slide stained with a counter-stain, and wherein the determining the control image includes the one or more artifacts comprises determining pixels in the control image fall outside of a color range associated with the counter-stain.

15. A non-transitory computer-readable medium storing instructions which, when executed by a processor of an image analysis system, cause the image analysis system to:
    access a field of view (FOV) of an immunohistochemistry (IHC) image of an IHC slide;
    access a control image of a control slide associated with the IHC slide;
    perform a registration operation to align the IHC image and the control image to a single coordinate system;

as a result of the IHC image and the control image being aligned to the single coordinate system based on the registration operation, identify a distance metric between an image object of the IHC image to a corresponding image object of the control image, wherein the image object of the IHC image and the corresponding image object of the control image correspond to a same tissue type;

determine that the identified distance metric is below a predefined threshold;

in response to determining that the distance is below the predefined threshold, determine that the IHC image and the control image are structurally similar;

in response to determining that the IHC image and the control image are structurally similar, map a region corresponding to the FOV of the IHC image to a corresponding region of the control image;

designate the corresponding region of the control image as a control FOV;

detect artifacts within the control FOV; and identify, based on the detected artifacts, a presence of artifacts within the FOV of the IHC image, wherein the artifacts correspond to pixels that are falsely identifiable as stained cells during an image analysis of the IHC image.

16. The non-transitory computer-readable medium of claim 15, wherein the control slide and the IHC slide include tissue sections from a same tissue block.

17. The non-transitory computer-readable medium of claim 15, wherein the registration operation includes transforming the IHC image or the control image using an affine transformation.

18. The non-transitory computer-readable medium of claim 15, wherein the control image is an image of a negative control slide stained with a counter-stain, and wherein the detecting the artifacts within the control FOV comprises determining pixels in the control FOV fall outside of a color range associated with the counter-stain.

19. The image analysis system of claim 1, wherein the determining the control image includes the one or more artifacts includes identifying a set of pixels having intensity values that are lower than a predefined threshold.

20. The image analysis system of claim 1, wherein:
the control image depicts a first tissue section of a biological sample; and
the IHC image depicts a second tissue section of the biological sample, wherein the first tissue section and the second tissue section are obtained from different slides of a same tissue block.

* * * * *